(12) United States Patent
Liu

(10) Patent No.: US 10,058,398 B2
(45) Date of Patent: Aug. 28, 2018

(54) TURBINE DENTAL DRILL MECHANISM AND TURBINE HEAD WITH SAME MOUNTED THEREIN

(71) Applicant: Zhengzhou Zezheng Technical Services Ltd., Zhengzhou, Henan (CN)

(72) Inventor: Xiaoxia Liu, Zhengzhou (CN)

(73) Assignee: ZHENGZHOU ZEZHENG TECHNICAL SERVICES LTD., Zhengzhou, Henan (CN)

( * ) Notice: Subject to any disclaimer, the term of this patent is extended or adjusted under 35 U.S.C. 154(b) by 281 days.

(21) Appl. No.: 14/373,779

(22) PCT Filed: Jan. 22, 2013

(86) PCT No.: PCT/CN2013/070837
§ 371 (c)(1),
(2) Date: Jul. 22, 2014

(87) PCT Pub. No.: WO2013/107431
PCT Pub. Date: Jul. 25, 2013

(65) Prior Publication Data
US 2015/0064649 A1    Mar. 5, 2015

(30) Foreign Application Priority Data

Jan. 22, 2012 (CN) .................. 2012 2 0034360 U
Sep. 14, 2012 (CN) .................. 2012 2 0489632 U
Sep. 28, 2012 (CN) .................. 2012 2 0527389 U

(51) Int. Cl.
*A61C 1/05* (2006.01)
*A61C 1/14* (2006.01)
*A61C 3/02* (2006.01)

(52) U.S. Cl.
CPC ................ *A61C 1/05* (2013.01); *A61C 1/141* (2013.01); *A61C 3/02* (2013.01)

(58) Field of Classification Search
CPC .............. A61C 1/05; A61C 3/02; A61C 1/141
(Continued)

(56) References Cited

U.S. PATENT DOCUMENTS 5,800,172 A * 9/1998 Goldenberg .............. A61C 1/05
433/132
2007/0087308 A1* 4/2007 Flock ..................... A61C 1/141
433/132

(Continued)

FOREIGN PATENT DOCUMENTS

| CN | 2829659 Y | 10/2006 |
| CN | 201159249 Y | 12/2008 |

(Continued)

OTHER PUBLICATIONS

International Search Report for Application No. PCT/CN2013/070837 dated Apr. 25, 2013.

*Primary Examiner* — Nicholas Lucchesi
(74) *Attorney, Agent, or Firm* — Hamre, Schumann, Mueller & Larson, P.C.

(57) ABSTRACT

A turbine dental drill mechanism, which includes a turbine and a turbine shaft. A balancing chamber is provided on the mechanism and includes an automatic balancing component provided therein. The automatic balancing component is a metal ball, sand grains or a flexible body. The metal ball in the balancing chamber can enhance the balance. The sand grains in the balancing chamber can reduce noise while also enhancing balance. The flexible body in the balancing chamber can eliminate noise and provide weight adjustment, thereby achieving automatic balancing.

6 Claims, 8 Drawing Sheets

(58) Field of Classification Search
USPC .................................................. 433/132, 133
See application file for complete search history.

(56) References Cited

U.S. PATENT DOCUMENTS

| | | | |
|---|---|---|---|
| 2009/0061384 A1 | 3/2009 | Thomssen et al. | |
| 2011/0306011 A1* | 12/2011 | Magneson | A61C 1/05 433/132 |
| 2013/0052606 A1* | 2/2013 | Brenann | A61C 1/003 433/27 |
| 2014/0038123 A1 | 2/2014 | Zhang et al. | |

FOREIGN PATENT DOCUMENTS

| | | | | |
|---|---|---|---|---|
| CN | 101524293 A | 9/2009 | | |
| CN | 101623213 A | 1/2010 | | |
| CN | 102379746 A | 3/2012 | | |
| CN | 202342207 U | 7/2012 | | |
| WO | 02054972 A1 | 7/2002 | | |
| WO | WO 2010135992 A1 * | 12/2010 | ............... | A61C 1/05 |
| WO | 2011147228 A1 | 12/2011 | | |

* cited by examiner

TURBINE DENTAL DRILL MECHANISM AND TURBINE HEAD WITH SAME MOUNTED THEREIN

CROSS-REFERENCE TO RELATED APPLICATIONS

The present application is a national phase entry under U.S.C. § 371 of International Application No. PCT/CN2013/070837 filed Jan. 22, 2013, which claims priority from Chinese Application Nos. 201220034360.X filed Jan. 22, 2012; 201220489632.5 filed Sep. 14, 2012; and 201220527389.1 filed Sep. 28, 2012, all of which are incorporated herein by reference.

FIELD OF THE INVENTION

The present invention relates to a major part used in dentistry—dental drill, and in particular to the mechanism inside a turbine dental drill head and the movement of the turbine head with said mechanism mounted therein.

DESCRIPTION OF THE PRIOR ART

Generally speaking, a head for an air-type cutting device used in dentistry is provided with a head part at the top thereof, the required parts of a cutting tool are installed inside the head part, including a rotor shaft of the cutting tool, two bearings for supporting a rotation shaft, and an impeller arranged between the two bearing parts, such that the high-pressure air supplied via an air supply passage arranged in a handle part of the head impacts the impeller to rotate the cutting tool. Wind wheel shaft and blades according to the prior art are all integrally injection molded parts. For example, according to the Invention Patent No. 200520045733.3, its wind wheel shaft and bur act in concert through a three-piece spring, and according to the Invention Patent Application No. 200910001394.1, a bur hole of its wind wheel shaft is arranged to be in the shape of a spline and to clamp a bur shaft via a plastic elastic clip; in addition, said patent is provided with a wind-resistant round piece to increase the rotational inertia. Other disposable dental drills utilize an interference fit between a bur hole and a bur shaft. Such structures require a special tool to load and unload the bur, and this has proven inconvenient. Although the Invention Patent Application 201020542727.X is also for a push button dental drill, it specifically comprises a wedge chuck within a wind wheel shaft, and the wedge chuck is used to clamp a bur. A connecting rod of the wedge chuck extends out of the wind wheel shaft and affixes a retaining board, while a disc spring is arranged between the retaining board and the wind wheel shaft on the outer periphery of the connecting rod, with a clamping force being provided by the disc spring. None of the above-described disposable dental drills has entered the stage of practical usage, for the reason that although China has several different factories producing disposable dental drills having an interference fit formed by an wind wheel shaft and a bur, the general accuracy of molds in China is 0.04 to 0.06 mm, and the accuracy for injection molded components is even poorer; in an environment of 300,000 revolutions per minute, therefore, the poor accuracy leads to imbalances, causing vibration and producing noise, which does not meet the standards, and they are not placed in practical use; the above-described two dental drills, in which pressure is used to load and unload the bur, have an even more complex structure, greater imbalance during rotation, and greater noise. Moreover, the prices of metal dental drills for repeated use at present are directly dependent on the machining precision, and the highest price difference is up to a hundredfold.

SUMMARY OF THE INVENTION

The object of the present invention is to solve the dynamic balance problem during high-speed rotation of the mechanism of the turbine dental drill according to the prior art.

The present invention is implemented in such a way: a turbine dental drill mechanism, comprising a turbine and a turbine shaft, a balancing chamber is provided on the mechanism, and an automatic balancing member is provided in the balancing chamber.

The automatic balancing member is a metal ball.

The automatic balancing member is sand grains.

The automatic balancing member is a flexible body.

The flexible body is a flexible colloid or a flexible hydrogel or a flexible foam plastic.

The flexible body is a flexible capsule with the structure thereof being that at least one of a liquid, a flexible colloid, a flexible hydrogel, a metal ball or sand grains is filled in a flexible shell.

The flexible shell is one of a flexible latex shell, a silica gel flexible shell or a flexible net-like shell.

The turbine and blades of the mechanism are a hollow structure surrounding the turbine shaft, and the hollow part is the balancing chamber.

A clamping jaw is arranged inside the turbine shaft of the mechanism, one end of the clamping jaw is connected to a clamping jaw rod, the clamping jaw rod extends out of a hole of the turbine shaft and is connected to a spring retaining board, the spring retaining board and the end of the turbine shaft are provided with a spring around the clamping jaw rod, the spring retaining board is of a hollow structure, and the hollow part is the balancing chamber.

A clamping jaw is arranged inside the turbine shaft of the mechanism, one end of the clamping jaw is connected to a clamping jaw rod, the clamping jaw rod extends out of a hole of the turbine shaft and is connected to a spring retaining board, the spring retaining board and the end of the turbine shaft are provided with a disc spring around the clamping jaw rod, and a ring-shaped balancing chamber is formed between the butterfly spring and the spring retaining board; or the spring retaining board and the end of the turbine shaft are provided with two locking disc springs around the clamping jaw rod, and a ring-shaped balancing chamber is formed between the two butterfly springs; the automatic balancing member is a ring shape that engages with the ring-shaped balancing chamber.

A dental drill head composed of a head housing, a wind wheel and a bearing, the wind wheel comprising a wind wheel shaft and wind wheel blades, a dynamic balancing hole being provided in the end of the wind wheel shaft, and a dynamic balancing body being arranged inside the dynamic balancing hole.

A wind wheel shaft hole is provided on the wind wheel shaft, a clamping jaw in the wind wheel shaft hole is connected to a clamping jaw rod, the end of the clamping jaw rod extends out of the wind wheel shaft hole and a dynamic balancing hole is provided in one end of the clamping jaw rod, and a dynamic balancing body is provided inside the dynamic balancing hole.

A flexible rubber or sponge is arranged between the dynamic balancing body and the dynamic balancing hole.

A spline hole is provided in the end of the wind wheel shaft with a spline inside the spline hole in a clearance fit, the spline extending out of the spline hole to fix a dynamic balancing plate.

A wind wheel shaft hole is provided on the wind wheel shaft, a clamping jaw in the wind wheel shaft hole is connected to a clamping jaw rod, the end of the clamping jaw rod extends out of the wind wheel shaft hole and a spline hole is provided in one end of the clamping jaw rod with a spline inside the spline hole in a clearance fit, and the spline extends out of the spline hole to fix a dynamic balancing plate.

The spline is a ball-shaped spline, the spline of the ball-shaped spline being distributed in an arc form along the axial direction of the turbine shaft on the ball surface; the spline hole engaging with the ball-shaped spline is a spherical cavity spline hole, and a spline groove is formed inside the spherical cavity spline hole for engaging with the ball-shaped spline.

A flexible rubber or sponge is arranged between the spline and the spline hole.

A turbine dental drill head composed of a head housing, a wind wheel and a bearing, the wind wheel comprising a wind wheel shaft and wind wheel blades, and the wind wheel shaft and wind wheel blades being of an integral structure.

A rubber member is arranged between the head housing and the wind wheel, in the natural state, the rubber member is in contact with both the head housing and the wind wheel, and in the working state, the rubber member is separated from one of the head housing and the wind wheel.

The rubber member refers to a rubber layer fixed on the inner side of a head cover of the head housing, the rubber layer forming a cavity with the head cover.

A through hole is formed on the head cover, and the through hole communicates with the cavity formed by the rubber layer and the head cover.

A braking plate is arranged at the end of the wind wheel shaft, in the natural state, the rubber layer is in contact with the braking plate, and in the working state, the rubber layer is separated from the braking plate A braking plate is arranged at the end of the wind wheel shaft, a ring-shaped groove I is formed on the braking plate, a rubber ring I is disposed inside the ring-shaped groove I, in the natural state, the rubber ring I is in contact with the head cover, and in the working state, the rubber ring I enters the groove as acted on by a centrifugal force and is separated from the head cover.

A ring-shaped groove II is arranged on the side of wind wheel blades of the wind wheel shaft, a rubber ring II is disposed inside the ring-shaped groove II, in the natural state, the rubber ring II is in contact with the bearing seat of the head housing, and in the working state, the rubber ring II enters the groove as acted on by a centrifugal force and is separated from the bearing seat.

A dynamic balancing hole is provided in the end of the wind wheel shaft, a dynamic balancing body is provided inside the dynamic balancing hole, and a flexible rubber or sponge is arranged between the dynamic balancing body and the dynamic balancing hole.

A spline hole is provided in the end of the wind wheel shaft with a spline inside the spline hole in a clearance fit, the spline extends out of the spline hole to fix a dynamic balancing plate, and a flexible rubber or sponge is arranged between the spline and the spline hole.

A clamping jaw hole is provided on the wind wheel shaft, a clamping jaw in the clamping jaw hole is connected to a clamping jaw rod, and a dynamic balancing hole or spline hole is provided on the clamping jaw rod.

The present invention that employs the above technical solution has the following advantages:

1. As a metal ball is arranged in the balancing chamber, the metal ball corrects imbalance through rolling when imbalance occurs to the high speed rotation, but causes high noise; the use of sand grains, in particular metal sand grains, lowers the noise while correcting imbalance. When a flexible body is used, the effective part of an automatic balancing member with the same weight for correcting imbalance is reduced, but there is no noise, the weight is adjusted, and automatic balancing can still be achieved.

2. The arrangement of a dynamic balancing body in the wind wheel shaft keeps the original external dimensions of the dental drill unchanged and performs automatic balancing on the imbalance of the rotating parts; a spline hole is provided with a spline inside the spline hole in a clearance fit, the spline extends out of one end of the wind wheel shaft to fix a dynamic balancing plate, the dynamic balancing plate can adjust dynamic balance in a wide range, even when there is a great degree of imbalance of the wind wheel, such as die cast parts, automatic adjustment can still be performed, thereby reducing the costs of high precision machining.

3. Since the pressing area is reduced and a cavity is formed between the rubber layer and the head cover, it is not easy for teeth to touch the pressing part. If they touch the pressing part once in a while, they will not touch the braking plate due to the provision of the cavity, which avoids the impact on the rotation speed; the arrangement of a rubber ring inside the ring-shaped groove not only prevents suckback, but also automatically adjusts dynamic balance, which attains two goals by a single move and lowers the cost. The arrangement of the dynamic balancing body in the wind wheel shaft maintains the original dimensions of the dental drill, a spline hole is provided with a spline inside the spline hole in a clearance fit, the spline extends out of one end of the wind wheel shaft to fix a dynamic balancing plate, such a structure can adjust dynamic balance in a wide range, even when there is a great degree of imbalance of the wind wheel, automatic adjustment can still be performed, thereby reducing the costs of high precision machining.

DETAILED DESCRIPTION OF SPECIFIC EMBODIMENTS

A turbine dental drill mechanism, comprising a turbine 1 and a turbine shaft 2, a balancing chamber 3 is provided on the mechanism, and an automatic balancing member is provided in the balancing chamber 3, wherein the balancing chamber 3 may be formed in the following ways.

Figure 1:
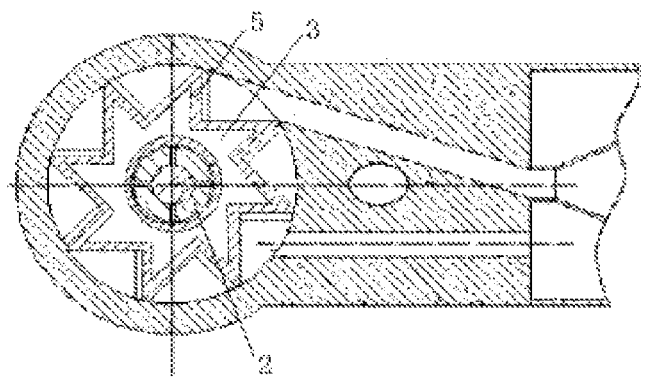
FIG. 1 illustrates the structure of the arrangement of a balancing chamber at the hollow part surrounding the turbine blades according to the present invention.

One, the turbine 1 and the turbine blades 5 of the mechanism according to the present utility model are a hollow structure surrounding the turbine shaft 2, the hollow part is the balancing chamber 3, and an automatic balancing member is provided in the balancing chamber 3, as shown in FIG. 1.

Figure 2:
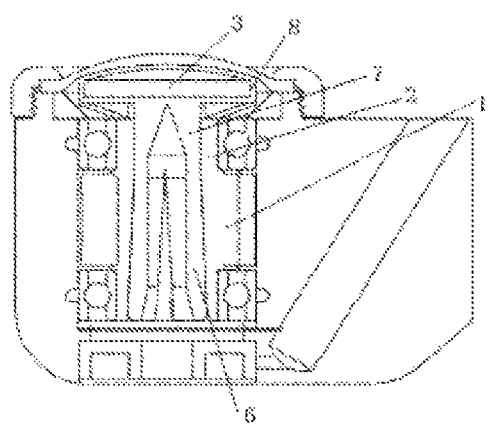
FIG. 2 illustrates the arrangement of a balancing chamber at the hollow part of the spring retaining board according to the present invention.
Figure 3:
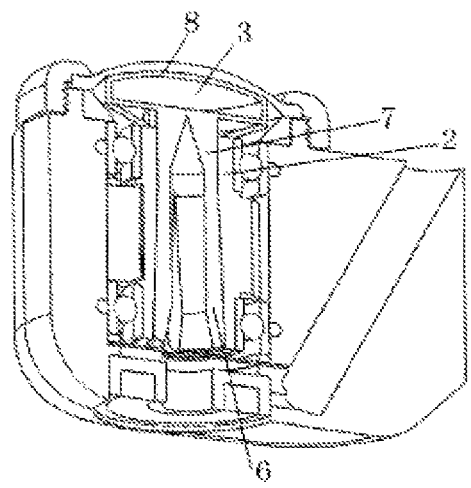
FIG. 3 is another view of the arrangement of a balancing chamber at the hollow part of the spring retaining board according to the present invention.

Two, a clamping jaw 6 is arranged inside the turbine shaft 2 of the mechanism, one end of the clamping jaw 6 is connected to a clamping jaw rod 7, the clamping jaw rod 7 extends out of a hole of the turbine shaft and is connected to a spring retaining board 8, the spring retaining board 8 and the end of the turbine shaft 2 are provided with a spring around the clamping jaw rod 7, the spring retaining board 8 is of a hollow structure, and the hollow part is the balancing chamber 3, as shown in FIG. 2 and FIG. 3.

Figure 4:
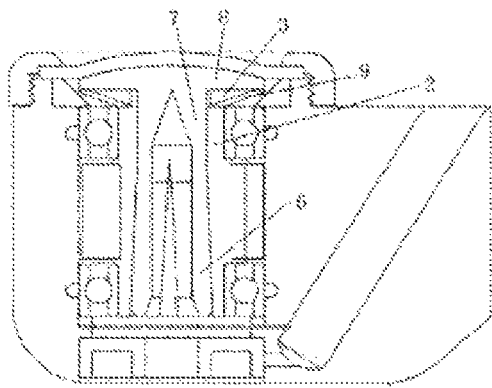
FIG. 4 illustrates the structure of the arrangement of a balancing chamber between the butterfly spring and the spring retaining board according to the present invention.
Figure 5:
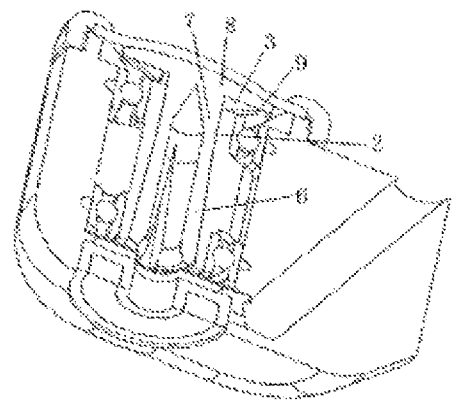
FIG. 5 illustrates another structure of the arrangement of a balancing chamber between the butterfly spring and the spring retaining board according to the present invention.
Figure 6:
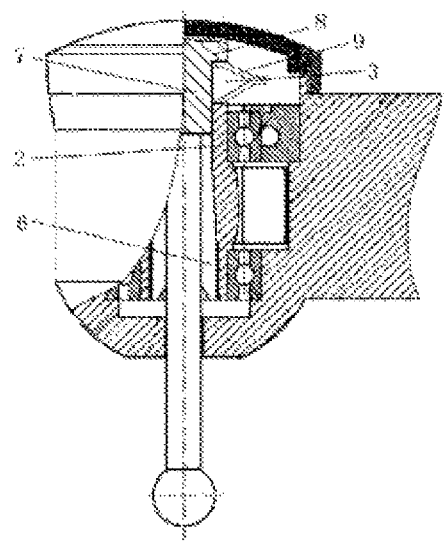
FIG. 6 illustrates the arrangement of a balancing chamber between two locking butterfly springs according to the present invention.

Three, a clamping jaw 6 is arranged inside the turbine shaft of the mechanism, one end of the clamping jaw 6 is connected to a clamping jaw rod 7, the clamping jaw rod 7 extends out of a hole of the turbine shaft and is connected to a spring retaining board 8, the spring retaining board 8 and the end of the turbine shaft 2 are provided with a disc spring 9 around the clamping jaw rod 7, and a ring-shaped balancing chamber 3 is formed between the butterfly spring 9 and the spring retaining board 8, as shown in FIG. 4 and FIG. 5; or the spring retaining board 8 and the end of the turbine shaft 2 are provided with two locking disc springs 9 around the clamping jaw rod 7, and a ring-shaped balancing chamber 3 is formed between the two butterfly springs 9; the automatic balancing member is a ring shape that engages with the ring-shaped balancing chamber, as shown in FIG. 6.

According to the present utility model, the automatic balancing member in the balancing chamber 3 may be a metal ball, or may be sand grains or metal sand grains.

Figure 7:
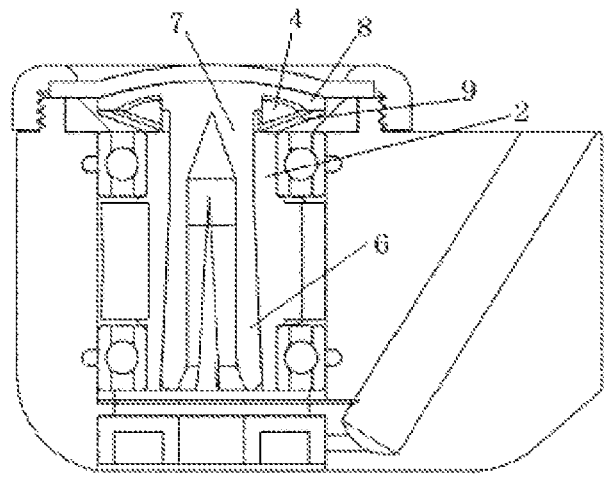
FIG. 7 illustrates the structure that the automatic balancing member is a flexible body according to the present invention.
Figure 8:
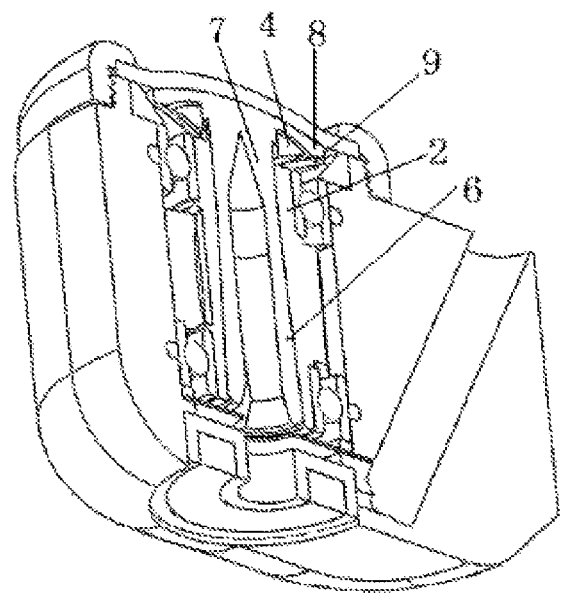
FIG. 8 illustrates another structure that the automatic balancing member is a flexible body according to the present invention.

As shown in FIG. 7 and FIG. 8, the automatic balancing member in the balancing chamber 3 may be further provided with a flexible body, the flexible body 4 is actually a flexible body that can change its shape when slightly acted on by a force, the center of gravity of the flexible body is changed by changing the shape of the flexible body, and ultimately the mechanism's automatic balancing can be achieved during high speed rotation. The flexible body can be fixed inside the balancing chamber 3, the ring-shaped cavity shown in FIG. 7 and FIG. 8 is expanded as the spring retaining board 8 concaves upwardly, for example, the bottom surface of the flexible body is fixed, the center of gravity of the flexible body is changed by swinging of the flexible body, thereby achieving the mechanism's automatic balancing during high speed rotation, since the bottom surface of the flexible body is fixed, when the mechanism is installed inside the head housing of the dental drill for use, the flexible body will not fall off even when the bottom surface of the flexible body rotates by 180 degrees and faces upward, which does not affect the mechanism's automatic balancing very much. The flexible body 4 may be of a pie shape or a ring shape; the material thereof includes but is not limited to capsules and filling materials used for breast prosthesis. Additionally, the center of gravity of the flexible body is coincident with the turbine shaft.

Specifically, the flexible body 4 may be a flexible colloid or a flexible hydrogel or a flexible foam plastic.

The flexible body 4 may also be a flexible capsule with the structure thereof being that at least one of a liquid, a flexible colloid, a flexible hydrogel, a metal ball or sand grains is filled in a flexible shell, wherein the provision of metal sand grains in the flexible capsule is the most preferred embodiment, since it can perform better automatic balancing. Moreover, the flexible shell is one of a flexible latex shell, a silica gel flexible shell or a flexible net-like shell, and the flexible net-like shell has a cloth-type structure.

When the mechanism is installed inside the head housing of the turbine dental drill, an automatic balancing turbine dental drill hand piece is formed.

Figure 9:
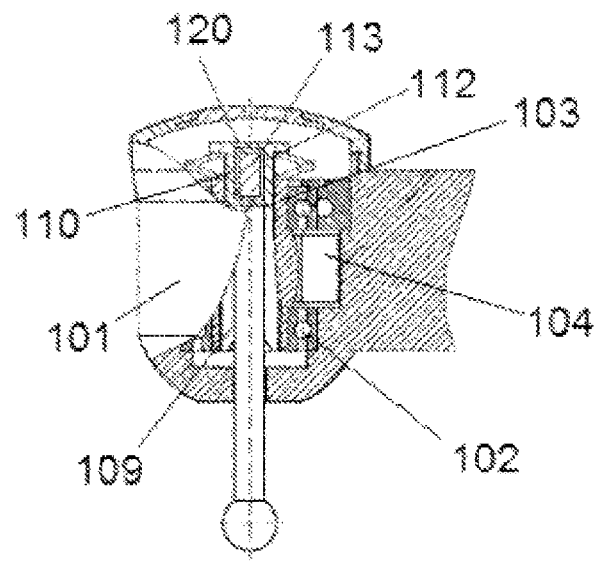
FIG. 9 illustrates the structure of the dynamic balancing body arranged according to the present invention.

FIG. 9 shows a dental drill head composed of a head housing 101, a wind wheel and a bearing 102, the wind wheel comprising a wind wheel shaft 103 and wind wheel blades 104, a wind wheel shaft hole is provided on the wind wheel shaft 103, a clamping jaw 109 arranged in the wind wheel shaft hole is connected to a clamping jaw rod 110, the end of the clamping jaw rod 110 extends out of the wind wheel shaft hole and a dynamic balancing hole 112 is provided in one end of the clamping jaw rod 110, and a dynamic balancing body 113 is encapsulated inside the dynamic balancing hole 112, a clearance fit is provided between the dynamic balancing body 113 and the dynamic balancing hole 112, and the dynamic balancing body 121 automatically adjusts the dynamic balance of the wind wheel through its radial movement inside the dynamic balancing hole 112. The dynamic balancing body 121 may be of a column shape, such as cylinder or prism, or may be ball shaped or have a shape of irregular particles.

A flexible rubber or sponge 120 is arranged between the dynamic balancing body 113 and the dynamic balancing hole 112, the flexible rubber is such as silica gel, polyurethane, etc., and the sponge is its foaming material. As a result, there is a flexible engagement between the dynamic balancing body 113 and the dynamic balancing hole 112.

The above embodiment describes the structure of dental drills in which pressure is used to load and unload the bur. For dental drills in which the bur is loaded and unloaded through plug or a key, a dynamic balancing hole 112 is arranged at the end of the wind wheel shaft, and a dynamic balancing body 113 is encapsulated inside the dynamic balancing hole 112, but a through hole is formed axially on the balancing body 113 that communicates with the bur hole or the key hole in the wind wheel shaft.

Figure 10:
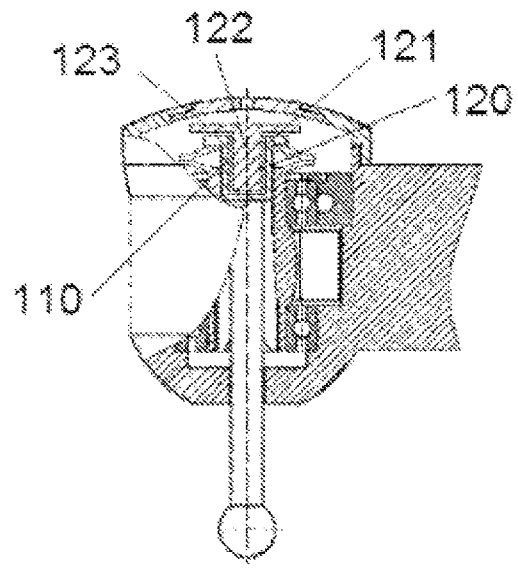
FIG. 10 illustrates the structure of the spline connection arranged according to the present invention.

As shown in FIG. 10, a spline hole 121 is provided in one end of the clamping jaw rod 110 with a spline 122 inside the spline hole 121 in a clearance fit, the spline 122 extending out of the spline hole 121 to fix a dynamic balancing plate 123, and a flexible rubber or sponge 120 is arranged between the spline 122 and the spline hole 121. The spline 124 automatically adjusts the dynamic balance of the wind wheel by driving the dynamic balancing plate to move radially through its radial movement inside the spline hole 123. Similarly, for dental drills in which the bur is loaded and unloaded through plug or a key, a spline hole 121 is provided in the end of the wind wheel shaft with a spline 122 inside the spline hole 121 in a clearance fit, the spline 122 extending out of the end of the wind wheel shaft to fix a dynamic balancing plate 123, but a through hole is formed axially on the spline 122 and the dynamic balancing plate 123 that communicates with the bur hole or the key hole in the wind wheel shaft. In such a way, the adjustment of dynamic balance is powerful, which can even adjust mechanisms die-cast with metal.

Figure 11:
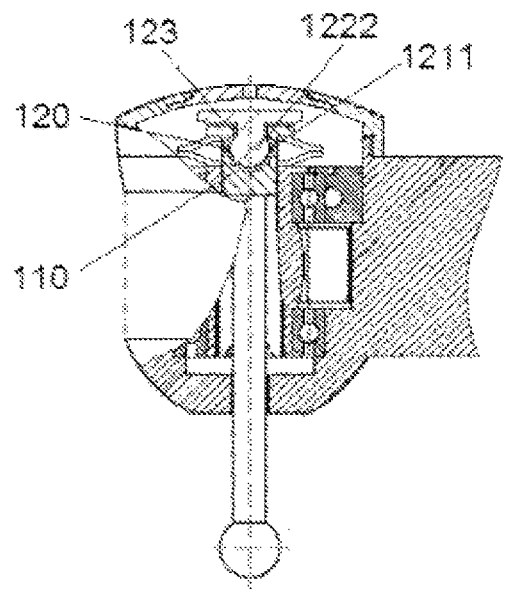
FIG. 11 illustrates the structure of the ball-shaped spline connection arranged according to the present invention.

As shown in FIG. 11, the spline is a ball-shaped spline 1222, the raised spline of the ball-shaped spline 1222 being distributed in an arc form along the axial direction of the turbine shaft on the ball surface; the spline hole engaging with the ball-shaped spline is a spherical cavity spline hole 1211, a spline groove is formed inside the spherical cavity spline hole 1211 for engaging with the ball-shaped spline, and the top portion of the ball-shaped spline 1222 extends out of the spherical cavity spline hole 1211 to fix a dynamic balancing plate 123. Such a structure can prevent the spline from disengaging out of the spline hole. This embodiment is similar to the utility model patent with the Chinese Patent No. 200720026788.9 and entitled "Tooth Type Universal Coupler", which can implement this embodiment with one ball.

The connection between the clamping jaw rod and the dynamic balancing plate is not limited to the above way, which can be implemented as long as the clamping jaw rod and the dynamic balancing plate are moveably connected.

A turbine dental drill head composed of a head housing 201, a wind wheel and a bearing 202, the wind wheel comprising a wind wheel shaft 203 and wind wheel blades 204, and the wind wheel shaft 203 and wind wheel blades 204 being of an integral structure.

Figure 12:
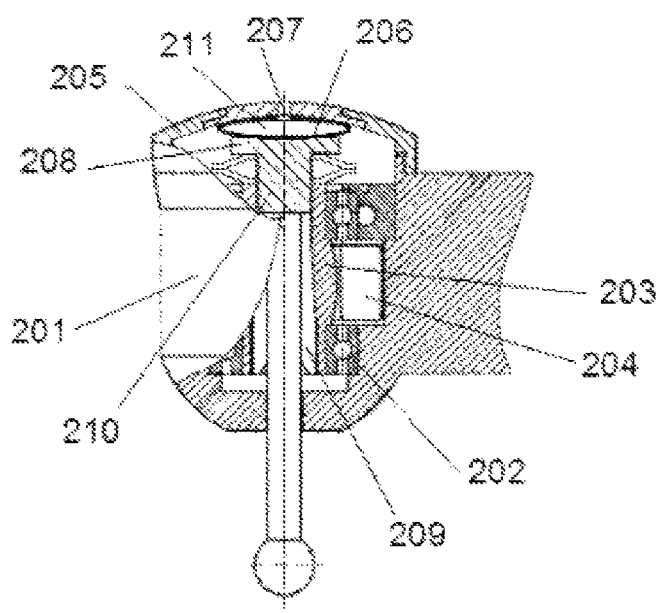
FIG. 12 illustrates the structure of the natural state of a rubber capsule fixed to the inner side of the pressing cover.
Figure 13:
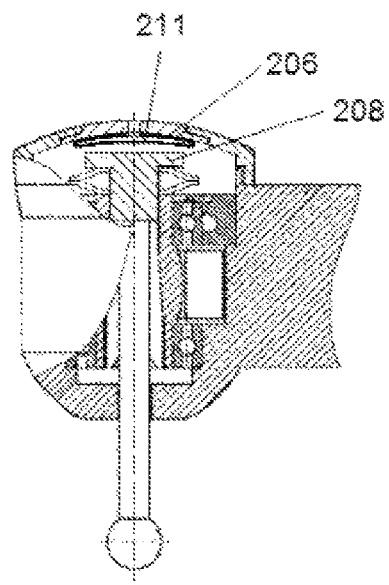
FIG. 13 illustrates the structure of the working state of a rubber capsule fixed to the inner side of the pressing cover.

As shown in FIG. 12 and FIG. 13, a rubber member is arranged between the head housing 201 and the wind wheel, in the natural state, the rubber member is in contact with both the head housing 201 and the wind wheel, and in the working state, the rubber member is separated from one of the head housing 201 and the wind wheel. The working state is that a high pressure gas is introduced into the head, the high pressure gas pushes the wind wheel to rotate, the rubber member is separated from one of the head housing and the wind wheel, and the wind wheel can rotate at high speed; stop the work, the supply of the high pressure gas stops, the rubber member is in contact with both the head housing and the wind wheel, and the wind wheel is braked to stop rotation, which can effectively prevent filth from being sucked back.

The above rubber member is that: a rubber layer 206 is fixed on the inner side of a head cover 205 of the head housing 201, the rubber layer 206 forming a cavity with the head cover 205. In the natural state, the rubber layer is in contact with the end of the wind wheel shaft, and in the working state, the rubber layer 206 is separated from the end of the wind wheel shaft as pressed by the air pressure in the head cover; stop the work, the supply of the high pressure gas stops, the rubber layer restores contact with the end of the wind wheel shaft, and the wind wheel is braked to stop rotation, which can effectively prevent filth from being sucked back.

A through hole 207 is formed on the head cover 205, and the through hole 207 communicates with the cavity formed by the rubber layer 206 and the head cover 205. At this moment, the rubber layer 206 and the head cover 205 forms the cavity for communicating with the atmosphere. It is favorable for the rubber layer to be separated from the end of the wind wheel shaft in the working state.

A braking plate 208 is arranged at the end of the wind wheel shaft 203, in the natural state, the rubber layer 206 is in contact with the braking plate 208, and in the working state, the rubber layer 206 is separated from the braking plate 208. Since the area of contact between the braking plate 208 and the rubber layer 206 is large, it is favorable for the wind wheel to be braked and to stop the rotation. For heads in which the bur is plugged or the bur is loaded and unloaded through a key, the braking plate 208 may be directly arranged at the end of the wind wheel shaft, and a through hole is formed in the center of the braking plate 208 for inserting a pin or key, which is not shown; FIG. 12 and FIG. 13 show a head in which pressure is used to load and unload the bur, a clamping jaw hole is provided on the wind wheel shaft 203, a clamping jaw 209 in the clamping jaw hole is connected to a clamping jaw rod 210, the clamping jaw rod 210 extends out of the end of the wind wheel shaft and a braking plate 208 is arranged. In such a circumstance, the corresponding head cover 205 is a pressing head cover, the pressing part for pressing the head cover is corresponding to the rubber layer 206, the rubber layer 206 may be a rubber capsule 211, the part of the rubber capsule 211 corresponding to the head cover is fixed with the head cover and does not affect the pressing, the other parts are the rubber layer, and of course, it may also be that the periphery of the rubber capsule 211 is fixed with the head cover, which divides the rubber capsule 211 into two surfaces with one surface as the pressing part of the head cover and the other surface as the rubber layer.

Figure 14:
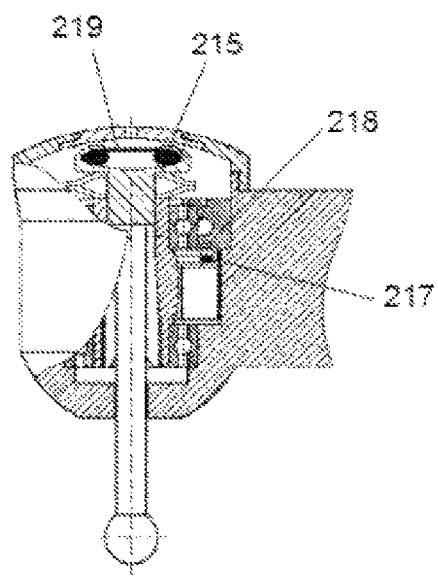
FIG. 14 illustrates the structure of the working state of a ring-shaped groove formed on the braking plate.
Figure 15:
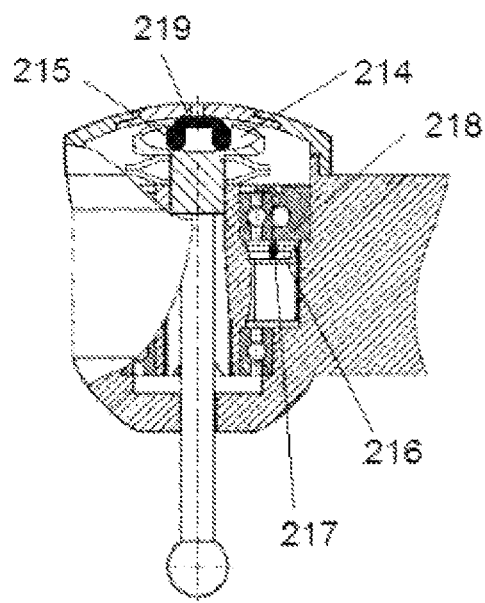
FIG. 15 illustrates the structure of the natural state of a ring-shaped groove formed on the braking plate.

As shown in FIG. 14 and FIG. 15, a braking plate 208 is arranged at the end of the wind wheel shaft, a ring-shaped groove I214 is formed on the braking plate 208, a rubber ring I215 is disposed inside the ring-shaped groove I214, in the natural state, the rubber ring I215 is in contact with the head cover 205, and in the working state, the rubber ring I215 enters the groove as acted on by a centrifugal force and is separated from the head cover 205. In such a way, the rubber ring I215 is capable of both braking and automatically adjusting the dynamic balance of the wind wheel. A rubber film 219 may be arranged on the rubber ring I215, which can increase the friction area for better braking.

A ring-shaped groove II216 is arranged on the side of wind wheel blades 204 of the wind wheel shaft 203, a rubber ring II217 is disposed inside the ring-shaped groove II216, in the natural state, the rubber ring II217 is in contact with the bearing seat 218 of the head housing 201 as shown in FIG. 15, and in the working state, the rubber ring II217 enters the groove as acted on by a centrifugal force and is separated from the bearing seat 218 as shown in FIG. 14, wherein the rubber ring II217 is capable of both braking and automatically adjusting the dynamic balance of the wind wheel. Ring-shaped grooves are arranged on the sides of both the end of the wind wheel shaft and the wind wheel blades in FIGS. 14 and 15. In fact, it is ok to arrange only one ring-shaped groove, which can of course be disposed on both sides of the wind wheel blades.

Figure 16:
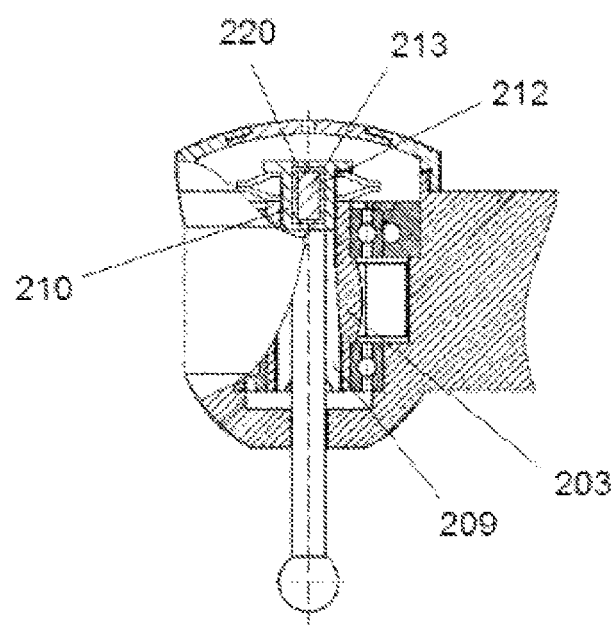
FIG. 16 illustrates the structure of the dynamic balancing body arranged in the wind wheel shaft.

As shown in FIG. 16, a dynamic balancing hole 212 is provided in the end of the wind wheel shaft, a dynamic balancing body 213 is provided inside the dynamic balancing hole 212, and a flexible rubber or sponge 220 is arranged between the dynamic balancing body 213 and the dynamic balancing hole 212. The flexible rubber is such as silica gel, polyurethane, etc. The dynamic balancing body 213 automatically adjusts the dynamic balance of the wind wheel through its radial movement inside the dynamic balancing hole 220. The dynamic balancing body 213 may be of a column shape, such as cylinder or prism, or may be ball shaped or have a shape of irregular particles.

Figure 17:
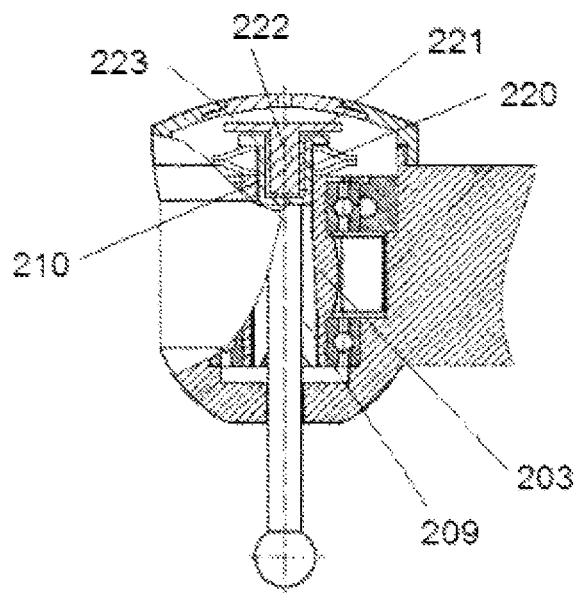
FIG. 17 illustrates the structure of spline engagement between the wind wheel shaft and the dynamic balancing plate.

As shown in FIG. 17, a spline hole 221 is provided in the end of the wind wheel shaft with a spline 222 inside the spline hole 221 in a clearance fit, the engagement between the spline 222 and the spline hole 221 may also be a structure of tooth-ball joint, and the tooth-ball joint is the tooth-ball joint according to the Patent No. 200720026788.9. The spline 222 extends out of the end of the wind wheel shaft to fix a dynamic balancing plate 223, and a flexible rubber or sponge 220 is arranged between the spline 222 and the spline hole 221. The spline 222 automatically adjusts the dynamic balance of the wind wheel by driving the dynamic balancing plate 223 to move radially through its radial movement inside the spline hole 223. The spline hole 221 and the spline 222 in FIG. 18 are a structure for preventing the spline 222 from disengaging out of the hole.

Figure 18:
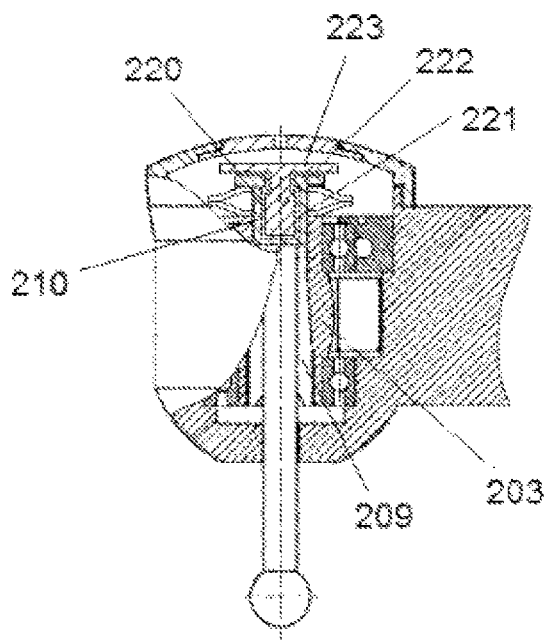
FIG. 18 illustrates the structure for preventing disengagement from the spline arranged between the wind wheel shaft and the dynamic balancing plate.

In FIG. 16, FIG. 17 and FIG. 18, a clamping jaw hole is arranged on the wind wheel shaft 203, the clamping jaw 209 in the clamping jaw hole is connected to a clamping jaw rod 210, and the clamping jaw rod 210 is provided with the dynamic balancing hole 212 or the spline hole 221. Such a circumstance is applicable for pressing dental drill hand pieces.

The present invention is not limited to the embodiment described above; any technical solution that is equivalent to the present invention or that is proposed by the present invention falls under the scope of the present invention.

The invention claimed is:

1. A turbine dental drill mechanism, comprising:
a turbine; and
a turbine shaft,
wherein a balancing chamber is provided on the mechanism and an automatic balancing member is provided in the balancing chamber,
the automatic balancing member is a flexible body,
a bottom surface of the flexible body is fixed inside the balancing chamber,
a center of gravity of the flexible body is changed by swinging the flexible body to achieve an automatic balancing of the mechanism during a high speed rotation of the mechanism, and
the flexible body is configured to change its shape when the flexible body is slightly acted upon by a force so that the center of gravity of the flexible body is changed and ultimately the automatic balancing of the mechanism is achieved during the high speed rotation of the mechanism.

2. The turbine dental drill mechanism as set forth in claim 1, wherein the flexible body is a flexible colloid, a flexible hydrogel, or a flexible foam plastic.

3. The turbine dental drill mechanism as set forth in claim 1, wherein the flexible body is a flexible capsule, the structure of the flexible capsule includes at least one of a liquid, a flexible colloid, a flexible hydrogel, a metal ball, or sand grains filled in a flexible shell.

4. The turbine dental drill mechanism as set forth in claim 3, wherein the flexible shell is one of a flexible latex shell, a silica gel flexible shell, or a flexible net-like shell.

5. The turbine dental drill mechanism as set forth in claim 4, further comprising blades, wherein the turbine and blades of the mechanism are a hollow structure surrounding the turbine shaft, and a hollow part is the balancing chamber.

6. A dental drill head, comprising:
a head housing;
a wind wheel; and
a bearing, the wind wheel including a wind wheel shaft and wind wheel blades,
wherein a dynamic balancing hole is provided in the end of the wind wheel shaft, and a dynamic balancing body is arranged inside the dynamic balancing hole, and
a flexible rubber or sponge is arranged between the dynamic balancing body and the dynamic balancing hole.

* * * * *